Patented May 2, 1944

Plant Pat. 626

UNITED STATES PATENT OFFICE

626

ROSE PLANT

Edward E. Marsh, Pasadena, Calif.

No Drawing. Application October 15, 1943,
Serial No. 506,319½

1 Claim. (Cl. 47—61)

This invention relates to a new and distinct variety of hybrid tea rose plant originating as a sport found on a bush plant of the well known "Christopher Stone" rose.

The dominating characteristics of this new rose are its strong and vigorous climbing form and its profuse blossoming and having no apparent tendency to revert to bush form when propagated by budding.

As regards its other characteristics, particularly color and form, no differences are notable as it follows the characteristic form of the "Christopher Stone" rose of the bush variety.

As is true of the bush "Christopher Stone" plants, the climbing plant of this invention produces semi-double flowers of a pleasing combination of scarlet and crimson. The buds are long-pointed, opening into a very large semi-double flower. As to its color characteristics, its foliage characteristics, its budding and bloom, it truly follows the bush variety of the well known "Christopher Stone" hybrid tea rose bush plant. and it is believed unnecessary to specifically illustrate these color characteristics of foliage, bud and flower, and for this reason no drawings are submitted with this application.

This sport and its characteristics were observed, and it propagation was determined by budding at Altadena, California, where the rose and the climbing rose reproduced by budding were grown outdoors during the year 1943.

What I claim is:

A new and distinct variety of hybrid tea rose plant, characterized as to novelty by its strong and vigorous climbing habit and the habit of producing profuse flowers in greater quantity than can be found on its bush parent, substantially as described.

EDWARD E. MARSH